United States Patent
Ritscher et al.

(10) Patent No.: US 7,130,678 B2
(45) Date of Patent: Oct. 31, 2006

(54) ADAPTIVE MEMORY PRIORITIZATION FOR IMPLANTED MEDICAL DEVICES

(75) Inventors: David E. Ritscher, Minneapolis, MN (US); Kevin T. Ousdigian, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 601 days.

(21) Appl. No.: 10/423,601

(22) Filed: Apr. 25, 2003

(65) Prior Publication Data

US 2004/0215270 A1    Oct. 28, 2004

(51) Int. Cl.
*A61B 5/432* (2006.01)

(52) U.S. Cl. .................. 600/523; 600/509; 607/59

(58) Field of Classification Search ............... 600/509, 600/523; 607/59
See application file for complete search history.

(56) References Cited

U.S. PATENT DOCUMENTS

| | | | |
|---|---|---|---|
| 4,583,553 A * | 4/1986 | Shah et al. | ............... 600/517 |
| 5,007,431 A * | 4/1991 | Donehoo, III | ............... 600/509 |
| 5,513,645 A | 5/1996 | Jacobson et al. | |
| 5,944,745 A | 8/1999 | Rueter | |
| 6,134,474 A | 10/2000 | Fischell et al. | |
| 6,526,314 B1 * | 2/2003 | Eberle et al. | ............... 600/523 |

* cited by examiner

*Primary Examiner*—Robert Pezzuto
*Assistant Examiner*—Yun Haeng Lee
(74) *Attorney, Agent, or Firm*—Girma Wolde-Michael; Daniel G. Chapik

(57) ABSTRACT

In general, the invention is directed towards techniques for adaptively prioritizing cardiac episode data in a memory of an implanted medical device (IMD). More specifically, the IMD receives new cardiac episode data, assigns each piece of data a priority value, and stores the data in a memory of the IMD. The IMD can further recalculate initial priority values assigned to stored cardiac episode data in response to subsequent cardiac episode data. In this manner, the prioritization scheme used by the IMD is adaptive, i.e., changes as more contextual information regarding the cardiac episode and subsequent cardiac episodes becomes available. Upon exceeding a memory capacity threshold, the IMD identifies the stored cardiac episode data with a lowest priority from the hierarchical priority relationship, and overwrites the identified portion of the stored cardiac episode data with the new cardiac episode data.

49 Claims, 5 Drawing Sheets

ADAPTIVE MEMORY PRIORITIZATION FOR IMPLANTED MEDICAL DEVICES

TECHNICAL FIELD

The invention relates to medical devices and, more particularly, to storage of cardiac episode data within medical devices.

BACKGROUND

Implanted medical devices, such as implanted pacemakers, defibrillators or cardioverters, are programmed to perform various functions in response to cardiac episode data measured by various physiological sensors. The response of the implanted medical devices to measured cardiac episode data and other physiological data can be tailored by a physician to suit the needs of individual patients. In order to determine whether the implanted medical device is programmed properly, the physician directs the device to store measured cardiac episode data in memory. The cardiac episode data is transmitted from the implanted medical device to an external programmer device, for review by the physician.

Implanted medical devices, however, have a limited memory capacity for storage of cardiac episode data, e.g., electrograms, markers, episode classifications and the like, as well as other pertinent information, such as delivered therapies. Due to the limited memory capacity, the implanted medical devices typically are programmed to store certain pieces of information, such as certain segments of episode data in order to conserve memory. The physician programs the implanted device, for example, to store episode data that would be most valuable to the physician in order to diagnose the patient's condition and adjust the settings of the implanted medical device to prevent future cardiac episodes. Ordinarily, the implanted medical device is programmed to overwrite segments of episode data previously stored in the memory with new episode data when the memory is full.

SUMMARY

In general, the invention is directed to techniques for storing cardiac episode data in an implanted medical device (IMD) using adaptive hierarchical prioritization. In accordance with the invention, the IMD selects which information to initially store, and later selectively overwrites previously stored cardiac episode data in accordance with priority information maintained in a hierarchical data structure. The IMD overwrites parts of the cardiac episode data associated with a lowest priority first. As memory space becomes scarcer, however, the IMD overwrites cardiac episode data for entire episodes. In this manner, the IMD initially stores more detailed cardiac episode data that is incrementally overwritten in order of priority as new cardiac episode data is received. The result is the storage of as much of the most pertinent data as is possible.

Initially, the IMD stores either all, or all higher-priority new cardiac episode data and defines a hierarchical priority relationship among separate cardiac episodes as well as among the cardiac episode data associated with each of the individual cardiac episodes. More specifically, the IMD receives cardiac episode data and assigns the cardiac episode data an initial priority value. In some embodiments, the IMD assigns the initial priority value to the cardiac episode data based on the type of cardiac episode detected. For example, the IMD assigns a larger initial priority value to a detected ventricular episode than a detected atrial episode due to the fact that ventricular episodes are generally more dangerous to a patient. As an example of prioritization of data within an episode, the IMD assigns an atrial electrogram a higher priority value than a ventricular electrogram for a cardiac episode that originates within an atrium of the heart, since this is the information more relevant to diagnosing this type of episode. The cardiac episode data received by the IMD includes, for example, electrograms, marker channel diagrams, therapy decision rule outcomes, rate of the cardiac episode, regularity of the cardiac episode, voltage of delivered therapy, number of delivered shocks or antitachycardia pacing, morphologies of electrograms, activity level of the patient, lead impedance measurements, pressures measurements within the heart, presence of ischemia or edema before, after or during the cardiac episode, absence of ischemia or edema before, after or during the cardiac episode, P-waves and R-waves, and the like.

The IMD determines whether the IMD has sufficient memory capacity to store the received cardiac episode data. When the IMD has sufficient memory capacity for storage of the cardiac episode data, the IMD stores the cardiac episode data in the memory. When the IMD does not have sufficient memory capacity for storage of the cardiac episode data, the IMD identifies previously stored cardiac episode data with the lowest priority and compares the priority value of the received cardiac episode data with the priority values of this previously stored cardiac episode data with the lowest priority. If any of the previously stored cardiac episode data has a lower priority than the priority of the new cardiac episode data, the IMD overwrites the previously stored cardiac episode data with the new cardiac episode data.

In addition, the IMD determines whether any priority values associated with previously stored cardiac episode data should be recalculated due to the received cardiac episode data. The IMD recalculates priority values of previously stored cardiac episode data in response to subsequent cardiac events. Subsequent cardiac events include successive detection of higher priority cardiac episodes, detection of repeated cardiac episodes, delivery of a therapy to treat the detected cardiac episode, a sudden change in pressure or other hemodynamic parameter, an indication that a patient fell, e.g., from sensors such as accelerometers within IMD10, input received from a patient activator, time frame since the cardiac episode data was detected, length of the episode or the like. For example, the IMD increases the initial priority value of a previously detected cardiac episode when it is quickly followed by a successive cardiac episode of high significance. For example, an atrial episode followed immediately by a ventricular episode increases the priority value of the atrial episode. In this manner, the priority values assigned to the cardiac episode data are adaptive, i.e., able to change as more contextual information becomes available.

Concurrently, the IMD refines the hierarchical priority relationship, e.g., the hierarchical data structure, according to the assigned priority values. In other words, as the IMD receives cardiac episode data and associates the cardiac data with priority values and data identifiers, the IMD also develops the hierarchical data structure that defines the hierarchical relationship. The hierarchical data structure arranges episode and data identifiers, e.g., pointers that point to portions of the stored cardiac episode data, to determine significance of a cardiac episode in relation to other detected cardiac episodes, and within the cardiac episode to determine the relative significance of individual pieces of cardiac episode data. This is done in a manor to maximize the clinically-relevant information that is retained.

Alternatively or additionally, the IMD compresses a portion of the stored cardiac episode data in order to store the received cardiac episode data. The IMD determines whether the cardiac data with the lowest priority can be compressed to a reduced resolution and, in turn, reduce necessary memory space such that the new cardiac episode data can be stored. The IMD, for example, can compress an electrogram signal and store the reduced resolution electrogram to increase the available memory space for the received cardiac episode data. In this manner, the IMD retains as much uncompressed data as possible, but stores the lower priority data with a lower resolution, i.e., greater compression.

Depending on when a physician interrogates the IMD, the information stored by the IMD varies significantly. For example, if the physician interrogates the IMD shortly after the last time the IMD was interrogated, there is a large amount of detailed information available. This might be similar to information which is seen in a Holter recording. In this case, the IMD can collect extra information including episode data during normal sinus rhythms, all A—A intervals and V—V intervals, and the like. However, if the physician does not interrogate the IMD for a longer period of time, e.g., a year, much of the detailed information has been overwritten, but there is still overview information available, as well as some detailed information about the most critical events. Thus, the final result is that the IMD optimizes the cardiac episode data stored in memory of the IMD to provide the most relevant information needed for understanding the medical condition of the patient and for improving future treatment.

Further, the IMD, when interrogated, sends all or a portion of the stored cardiac episode data to the programmer or monitor in accordance with the hierarchical priority relationship. In other words, the IMD transmits the stored cardiac episode data with the highest priority to the programmer first followed by the stored cardiac episode data with a lower priority. In this manner, the IMD provides the physician or other reviewer with the most relevant cardiac episode data first. The IMD can further include a mechanism for tracking which cardiac episode data has been transferred. Upon transmitting the cardiac episode data, the IMD reduces the priority values of the cardiac episode data that has been transmitted to the programmer thereby allowing it to be overwritten as new cardiac episode data is received. This way, cardiac episode data with lower initial priority values may be stored because the higher priority cardiac episode data has already been transmitted to the programmer.

In one embodiment, the invention provides a method comprising assigning cardiac episode data initial priority values, storing the cardiac episode data in a memory associated with an implanted medical device, recalculating at least one of the initial priority values assigned to the cardiac episode data in response to subsequent cardiac episode data, and overwriting a portion of the stored cardiac episode data with new cardiac episode data according to a hierarchical priority relationship.

In another embodiment, the invention provides a computer-readable medium comprising instructions that cause a processor to assign cardiac episode data initial priority values, store the cardiac episode data in a memory associated with an implanted medical device, recalculate at least one of the initial priority values assigned to the cardiac episode data in response to subsequent cardiac episode data, and overwrite a portion of the stored cardiac episode data with new cardiac episode data according to a hierarchical priority relationship.

In another embodiment, the invention provides an implantable medical device comprising a memory to store cardiac episode data and a processor to assign cardiac episode data initial priority values, store the cardiac episode data in the memory, recalculate at least one of the initial priority values assigned to the cardiac episode data in response to subsequent cardiac episode data, and overwrite a portion of the stored cardiac episode data with new cardiac episode data according to a hierarchical priority relationship.

The details of one or more embodiments of the invention are set forth in the accompanying drawings and the description below. Other features, inventive aspects and advances of the invention will be apparent from the description and drawings, and from the claims.

DETAILED DESCRIPTION

Figure 1:
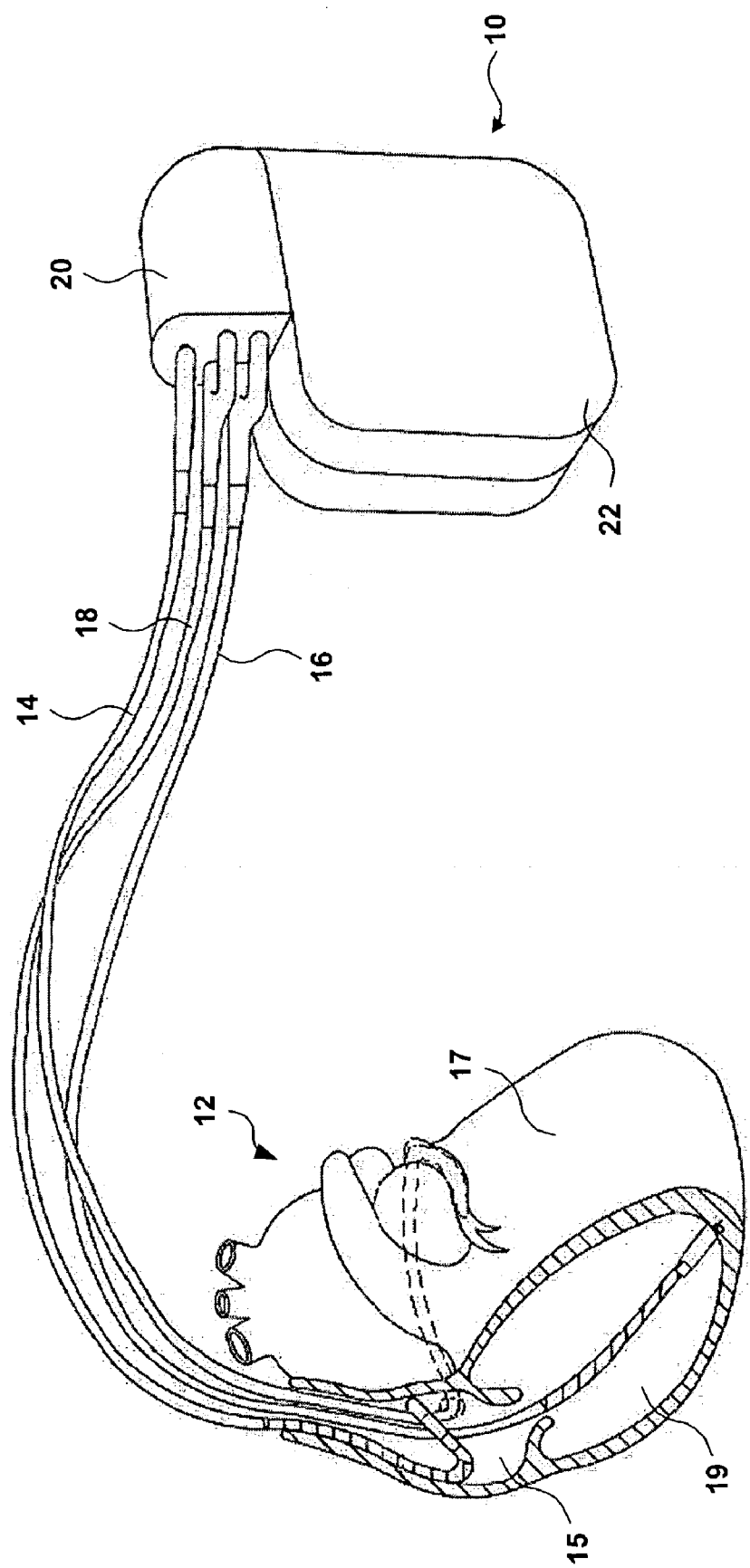
FIG. 1 is a schematic diagram illustrating an exemplary implanted medical device (IMD) shown in conjunction with a human heart.

FIG. 1 is a schematic diagram illustrating an exemplary implanted medical device (IMD) 10 shown in conjunction with a human heart 12. As will be described below, IMD 10 selectively stores episodic information according to a hierarchical priority relationship. Although a three-chamber IMD 10 and lead system is illustrated in FIG. 1 for purposes of illustration, methodologies implemented according to the present invention may be adapted for use with single chamber, dual chamber, or multi-chamber ICD or pacemaker systems, or cardiac monitoring devices. In addition, IMD 10 may include antitachycardia pacing, cardioversion, and defibrillation functionality in addition to pacing functionality. For instance, IMD 10 can be a pacemaker-cardioverter-defibrillator (PCD). Although the invention can also find application in numerous other types of IMDs or external medical devices, the specific structure of IMD 10 is described herein for purposes of example.

In the example of FIG. 1, IMD 10 includes a left ventricular (LV) coronary sinus lead 14, which is passed through the superior vena cava into right atrium 15 of heart 12, into the coronary sinus and then inferiorly in the great vein and cardiac veins extending from the coronary sinus to extend distal ring and tip electrodes alongside a left ventricle 17 of heart 12. The distal end of LV coronary sinus lead 14 positions the ring and tip electrodes with respect to the adjacent wall of left ventricle 17.

A right ventricular (RV) lead 16 is passed through the superior vena cava that leads into right atrium 15 and feeds into a right ventricle 19 of heart 12 where its distal ring and tip electrodes are fixed in place in the apex or in the interventricular septum.

A right atrial (RA) lead 18 is positioned within right atrium 15, with a distal end of RA lead 18 positioning the ring and tip electrodes with respect to the adjacent wall of the right atrium 15 or positioned within the atrial appendage. The electrodes of the different leads can be used for pacing and sensing as well as cardioversion or defibrillation. LV lead 14, RV lead 16 and RA lead 18 are inserted into a connector block 20 associated with IMD 10. IMD 10 has an outer housing 22.

IMD 10 obtains cardiac episode data via electrodes deployed on one or more of leads 14, 16, 18. In accordance with the invention, IMD 10 selectively overwrites episodic information according to a hierarchical priority relationship to efficiently use memory resources within the IMD. IMD 10 is programmed to store cardiac episode data in a memory and overwrite a portion of the stored cardiac episode data with new cardiac episode data according to the hierarchical priority relationship. More specifically, IMD 10 receives new cardiac episode data and assigns each piece of cardiac episode data a priority value. In some embodiments, IMD 10 recalculates initial priority values assigned to the stored cardiac episode data in response to the receipt of subsequent cardiac episode data. In this manner, the prioritization scheme used by IMD 10 is adaptive. In other words, the priority values of the stored cardiac episode data changes as more contextual information regarding the cardiac episode and subsequent cardiac episodes become available. Consequently, in view of memory limitations, IMD 10 is able to intelligently store information that is more useful to the physician upon interrogation of the IMD.

Upon exceeding a memory capacity threshold, IMD 10 identifies at least a portion of the stored cardiac episode data with a lowest priority from the hierarchical priority relationship, and overwrites the identified portion of the stored cardiac episode data with the new cardiac episode data when the priority value of the new cardiac episode data exceeds a priority value of the identified portion of the stored cardiac episode data.

Figure 2:
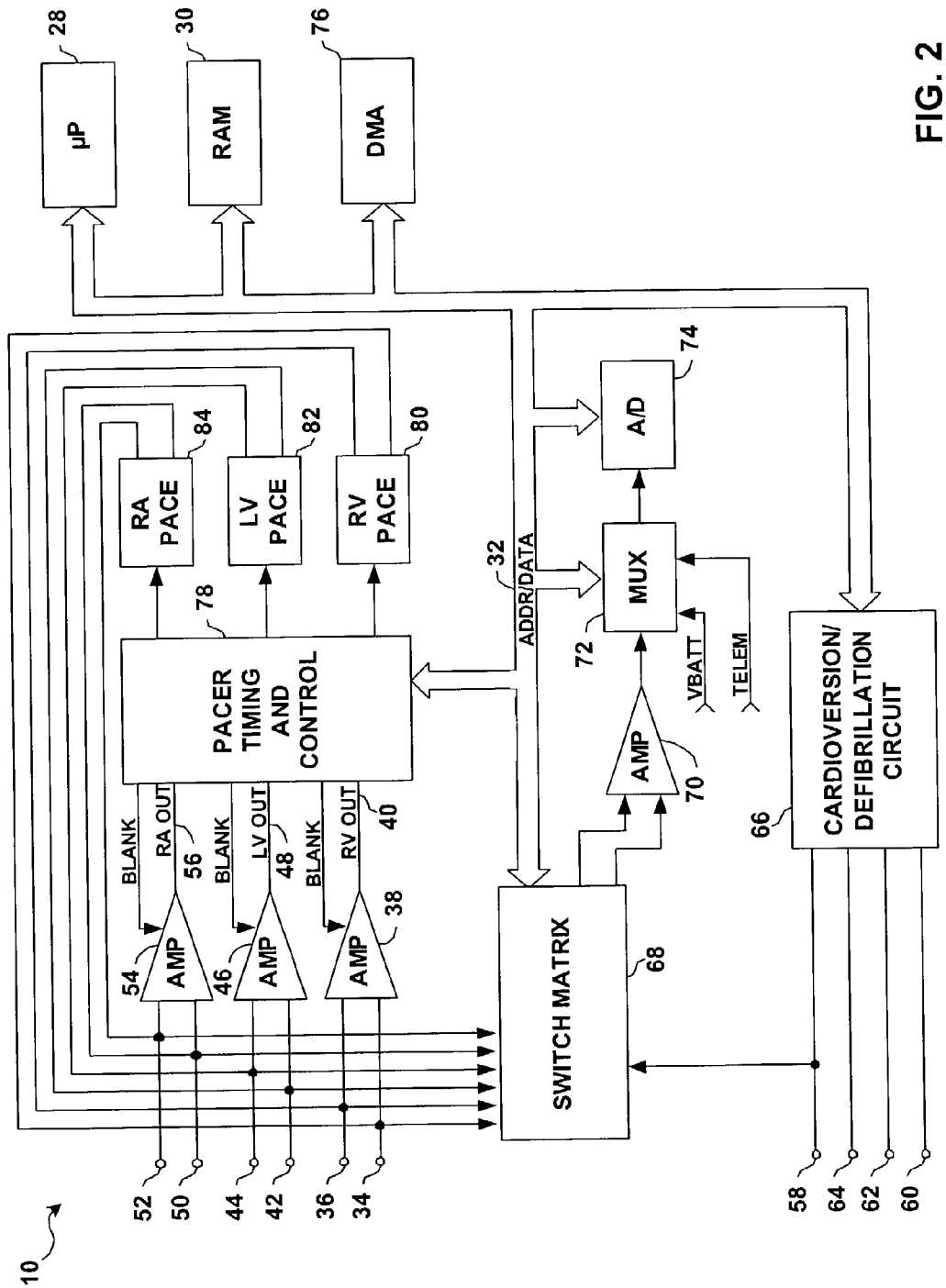
FIG. 2 is a functional block diagram of an embodiment of an IMD.

FIG. 2 is a functional block diagram of an embodiment of IMD 10, such as that shown in FIG. 1, in which IMD 10 comprises a pacemaker that includes pacing, defibrillation, and cardioversion functionality. The diagram of FIG. 2 should be taken as exemplary of the type of device in which various embodiments of the present invention may be embodied, and not as limiting, as the invention could be practiced in a wide variety of device implementations, including devices that provide pacing therapies but do not provide cardioversion and/or defibrillation therapy, and devices that provide no therapy at all, such as an implantable loop recorder.

In the example of FIG. 2, IMD 10 includes a microprocessor 28 that executes program instructions stored in memory, such as a read only memory (ROM) (not shown), an electrically erasable programmable read-only memory (EEPROM) (not shown), and/or a random access memory (RAM) 30, which control microprocessor 28 to perform the functions ascribed to microprocessor 28 herein. Microprocessor 28 is coupled to various other components of IMD 10 via an address/data bus 32 to communicate with and/or control those components.

As shown in FIG. 2, IMD 10 includes an electrode system for receiving cardiac data from heart 12 as well as providing therapy to heart 12. Electrodes 34 and 36 are coupled to amplifier 38. Amplifier 38 includes an automatic gain controlled amplifier providing an adjustable sensing threshold as a function of measured R-wave amplitude. Electrodes 34 and 36 are positioned proximate to a distal end of RV lead 16 (FIG. 1). A signal is generated on RV out line 40 whenever the signal sensed between electrodes 34 and 36 exceeds the present sensing threshold.

Electrodes 42 and 44 are coupled to amplifier 46, which also can take the form of an automatic gain controlled amplifier providing an adjustable sensing threshold as a function of measured R-wave amplitude. For instance, electrodes 42 and 44 are positioned proximate to a distal end of LV coronary sinus lead 14 (FIG. 1). A signal is generated on LV out line 48 whenever the signal sensed between electrodes 42 and 44 exceeds the present sensing threshold.

Electrodes 50 and 52 are coupled to amplifier 54, which can take the form of an automatic gain controlled amplifier providing an adjustable sensing threshold as a function of measured P-wave amplitude. In one example, electrodes 50 and 52 are positioned proximate to distal end of RA lead 18 (FIG. 1). A signal is generated on RA out line 56 whenever the signal between electrodes 50 and 52 exceeds the present sensing threshold.

IMD 10 further includes a can electrode 58, which is formed by an uninsulated portion of housing 22 of IMD 10. IMD 10 further includes elongated coil electrodes 60, 62, and 64. Coil electrodes 60, 62, and 64 are positioned along one or more of leads 14, 16, and 18. Can electrode 58 and coil electrodes 60, 62 and 64 are coupled to cardioversion/defibrillation circuit 66. Cardioversion/defibrillation circuit 66 includes energy storage circuits such as capacitors, switches for coupling the storage circuits to electrodes 58, 60, 62 and 64, and logic for controlling the coupling of the storage circuits to the electrodes to create pulses with desired polarities and shapes.

Switch matrix 68 is used to select which of the available electrodes are coupled to wide band (0.5–200 Hz) amplifier 70 for use in digital signal analysis. Selection of electrodes is controlled by microprocessor 28 via data/address bus 32, and the selections are varied as desired. Signals, i.e., cardiac episode data, from the electrodes selected for coupling to band pass amplifier 70 are provided to multiplexer 72, and thereafter converted to multi-bit digital signals by A/D converter 74, for storage in RAM 30 under control of direct memory access circuit (DMA) 76. Microprocessor 28 can employ digital signal analysis techniques to characterize the digitized signals stored in RAM 30 to recognize and classify the patient's heart rhythm. Microprocessor 28 further stores the results of the digital signal analysis, which also comprises cardiac episode data, in RAM 30.

In accordance with the invention, microprocessor 28 selectively overwrites episodic information according to a hierarchical priority relationship, thereby conserving memory resources. More specifically, microprocessor 28 receives new cardiac episode data and assigns each piece of cardiac episode data a priority value. Microprocessor 28 stores the cardiac episode data in a memory of IMD 10, e.g., RAM 30. Microprocessor 28 can further recalculate initial priority values assigned to the stored cardiac episode data in response to subsequent cardiac episode data. In this manner, the prioritization scheme used by microprocessor 28 is adaptive. In other words, the priority values of the stored cardiac episode data changes as more contextual information regarding the cardiac episode and subsequent cardiac episodes become available. Upon exceeding a memory capacity threshold, microprocessor 28 identifies at least a portion of the stored cardiac episode data with a lowest priority from the hierarchical priority relationship, and overwrites the identified portion of the stored cardiac episode data with the new cardiac episode data when the priority value of the new cardiac episode data exceeds a priority value of the identified portion of the stored cardiac episode data.

The remainder of the circuitry in the example of FIG. 2 is dedicated to delivery cardiac pacing, cardioversion and defibrillation therapies, which is responsive to data obtained by IMD 10 via leads 14, 16, and 18. Pacer timing/control circuitry 78 includes programmable digital counters, which control the basic time intervals associated with modes of pacing. Pacer timing/control circuitry 78 also controls escape intervals associated with pacing. Pacer timing/control circuitry 78 also determines the amplitude of the cardiac pacing pulses under control of microprocessor 28.

During pacing, escape interval counters within pacer timing/control circuitry 78 are reset upon sensing of R-waves as indicated by a signal on lines 40 and 48. In accordance with the selected mode of pacing, pacer timing/control circuitry 78 triggers generation of pacing pulses by pacer output circuitry 80, 82 and 84 which are coupled to electrodes 34, 36, 42, 44, 50 and 52.

The embodiment shown in FIG. 2 is merely exemplary. For example, the embodiment shown in FIG. 2 can be modified to include additional features, or adapted to other embodiments. In particular, the embodiment in FIG. 2 may be modified for an implanted medical device having electrodes mounted on any number of leads not shown in FIG. 1, or may not include one or more of the leads shown in FIG. 1. The embodiment shown in FIG. 2 can, for example, be modified to detect activity in or near the left atrium of the patient. The invention can find wide application to any form of implantable electrical device or possibly external medical devices that make use of selective data storage. Moreover, although described herein in the context of microprocessor based IMD 10, in some embodiments the invention is embodied in various IMDs that include one or more processors, such as microprocessors, DSPs, FPGAs, or other digital logic circuits.

Figure 3:
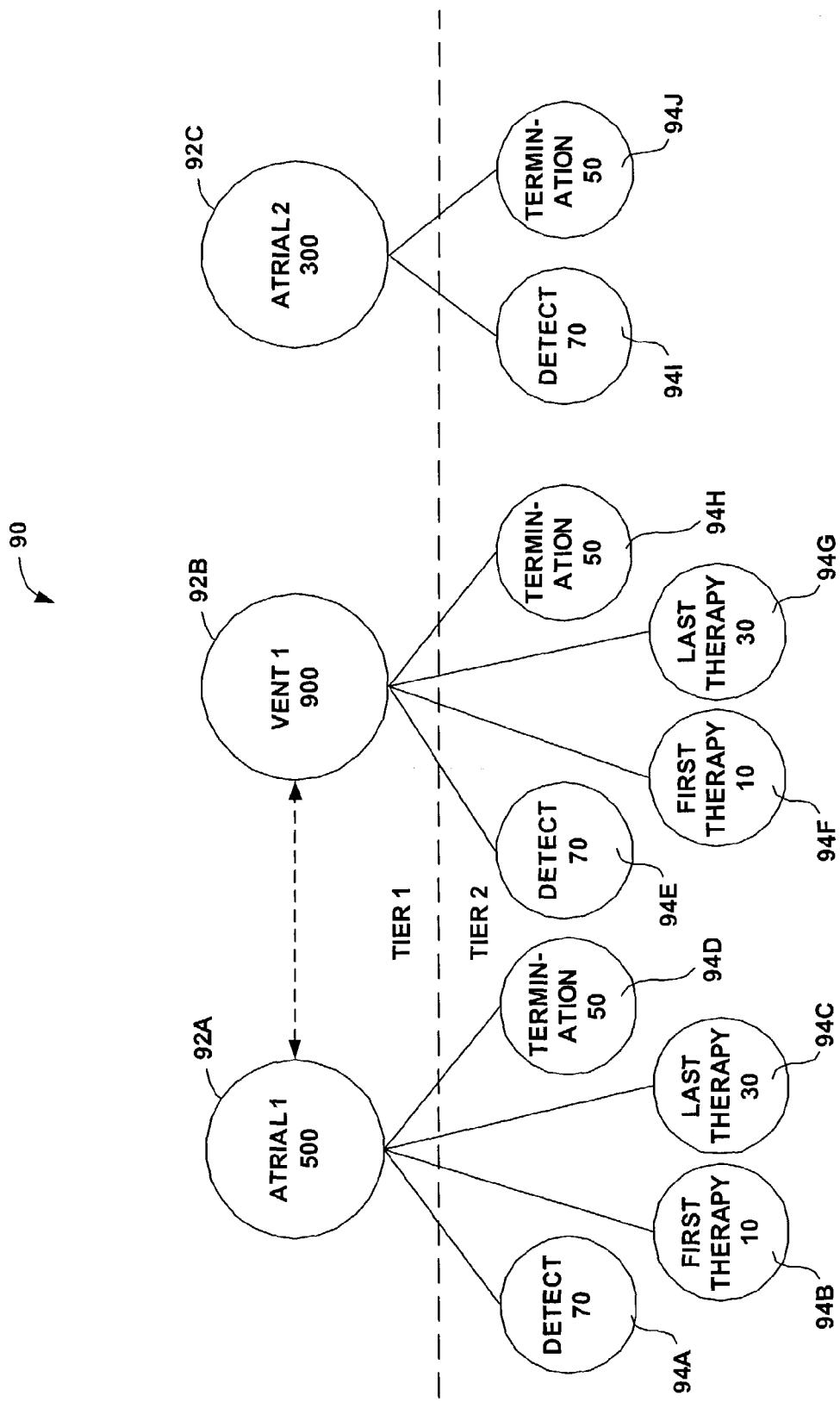
FIG. 3 is a schematic diagram illustrating an exemplary hierarchical data structure defining a hierarchical priority relationship.

FIG. 3 is a schematic diagram illustrating an exemplary hierarchical data structure 90 defining a hierarchical priority relationship. In accordance with the invention, IMD 10 selectively overwrites previously stored cardiac episode data in accordance with priority information maintained in hierarchical data structure 90.

Hierarchical data structure 90 includes base nodes 92A–92C (hereinafter 92) that make up a first tier (TIER 1) of hierarchical data structure 90 and episode nodes 94A–94J (hereinafter 94) that make up a second tier (TIER 2) of hierarchical data structure 90. Episode nodes 94 branch off respective base nodes 92. Specifically, episode nodes 94A–94D branch off of base node 92A, episode nodes 94E–94H branch off base node 92B and episode nodes 94I–94J branch off base node 92C. In this manner, each base node 92 and associated episode nodes 94 can be viewed as a tree structure, with base node 92 being a "root" of the tree structure and each episode node 94 being a "branch" of the tree structure. Although FIG. 3 is described in terms of a two-tier hierarchical data structure, hierarchical data structure 90 can have more than two tiers. For example, in some embodiments, hierarchical data structure 90 includes episode sub-nodes that branch off respective episode nodes 94 to make up a third tier, a fourth tier and so forth.

Each of base nodes 92 corresponds to a detected cardiac episode. Accordingly, each of the tree structures of hierarchical data structure 90 corresponds to a detected cardiac episode. In other words, microprocessor 28 associates a new base node 92 with the detected cardiac episode, thus creating a new tree structure within hierarchical data structure 90 for the detected cardiac episode. Specifically, in the example illustrated in FIG. 3, base node 92A corresponds to a first detected atrial episode (ATRIAL 1), base node 92B corresponds to a first detected ventricular episode (VENT 1) and base node 92C corresponds to a second detected atrial episode (ATRIAL 2), independent of the first detected atrial episode. The atrial and ventricular episodes include any sort of cardiac episode that originates in the respective chambers. For instance, atrial episodes, e.g., cardiac episodes corresponding to base nodes 92A and 92C, can include atrial tachycardias, atrial fibrillations, atrial flutters, premature atrial contractions, or other cardiac episodes originating in the atrium. Similarly, ventricular episodes, e.g., the cardiac episode corresponding to base node 92B, can include ventricular tachycardia, ventricular brachycardia, ventricular fibrillation, premature ventricular contractions, or other cardiac episodes originating in one of the ventricles.

Episode nodes 94 correspond to portions of the cardiac episode data of the cardiac episode associated with a corresponding base node 92. In the example illustrated in FIG. 3, episode nodes 94 correspond to cardiac episode data at different time intervals during the detected cardiac episode. Episode nodes 94 form branches of the tree structures and correspond to cardiac episode data associated with detection of the respective cardiac episode, one or more therapies applied to treat the respective cardiac episode, a termination of the respective cardiac episode, or the like.

In the example of FIG. 3, base node 92A includes branch episode nodes 94A–94D that correspond to cardiac episode data associated with detection of the cardiac episode (DETECT), application of a first therapy (FIRST THERAPY), application of a last therapy (LAST THERAPY) and termination of the detected cardiac episode (TERMINATION), respectively. The cardiac episode data associated with episode nodes 94 includes, for example, electrograms, marker channel diagrams, decision rule outcomes, rate of the cardiac episode, regularity of the cardiac episode, voltage of delivered therapy, number of delivered shocks, or the like. However, cardiac episode data associated with episode nodes 94 may include other types of cardiac episode data including morphologies of electrograms, activity level of the patient, lead impedance measurements, pressures measured within the heart, presence of ischemia or edema before, after or during the cardiac episode, absence of ischemia or edema before, after or during the cardiac episode, P-waves and R-waves.

Each of the nodes, i.e., base nodes 92 as well as episode nodes 94, includes identifiers that associate the nodes with at least a portion of the cardiac episode data stored in memory, e.g., RAM 30. More particularly, base nodes 92 include episode identifiers that correspond to cardiac episode data of a detected cardiac episode. For example, base node 92A includes an episode identifier that associates base node 92A with all of the cardiac data of the first detected atrial episode. Episode nodes 94 also include identifiers that associate episode nodes 94 with portions of cardiac episode data. Specifically, episode nodes 94 include data identifiers that associate respective episode nodes 94 with portions of the cardiac episode data associated with a corresponding base node 92. In other words, the data identifiers of episode nodes 94 correspond to a subset of cardiac episode data associated with episode identifiers of base nodes 92.

Episode node 94A, for example, includes a data identifier that associates episode node 94A with a detection portion of the cardiac episode data of the first detected atrial episode. The detection portion of the cardiac episode data of the first detected atrial episode can include electrograms obtained at detection, marker channel diagrams obtained at detection, and the like. Thus, data identifiers of episode nodes 94A–94D correspond to more specific portions of cardiac episode data than the episode identifier associated with node 92A. In this manner, the data identifiers facilitate overwriting and/or elimination of more discrete portions of cardiac episode data. The data and episode identifiers can, for example, be pointers that point to particular locations in memory where portions of cardiac episode data are stored. The identifiers reduce the need to shift data around within the memory of IMD 10. In addition, the higher priority cardiac episode data can be stored in a different location within the memory of IMD 10 than lower priority cardiac episode data to facilitate overwriting and/or elimination of cardiac episode data with a reduced need to move data around within the memory of IMD 10.

Each of base nodes 92 and episode nodes 94 further include an associated priority value used to prioritize cardiac episode data within hierarchical data structure 90. As will be described in further detail, the associated priority values are used to prioritize cardiac episode data within a respective tree structure as well as among other tree structures. Specifically, base nodes 92 have higher priority values than episode nodes 94 in order to support elimination of discrete pieces of cardiac episode data instead of data corresponding to an entire cardiac episode.

For example, base node 92A is assigned a priority value of 500 and episode nodes 94A–94D are assigned priority values of 70, 10, 30 and 50, respectively. Cardiac episode data corresponding to the data identifiers of episode nodes 94 will be overwritten due to a lower priority instead of overwriting the cardiac episode data corresponding to the entire cardiac episode, e.g., the cardiac episode data associated with the episode identifier of base node 92A. Further, the priority values assigned to the nodes are adaptive. In other words, the priority values change as more contextual information regarding the cardiac episode and subsequent cardiac episodes become available.

Initially, IMD 10 stores either all, or all higher-priority received cardiac episode data and defines a hierarchical priority relationship, e.g., hierarchical data structure 90, among the cardiac episode data. However, as the available memory capacity of IMD 10 begins to diminish, IMD 10 begins to selectively overwrite a portion of the stored cardiac episode data with new cardiac episode data according to the hierarchical priority relationship defined by hierarchical data structure 90. In general, IMD 10 overwrites parts of stored cardiac episode information associated with an episode of lower priority. As space becomes scarcer, however, entire episode trees are potentially overwritten.

Microprocessor 28 receives cardiac episode data and assigns the cardiac episode data an initial priority value. As will be described, microprocessor 28 successively receives cardiac episode data associated with a detected cardiac episode from different electrodes, algorithms executed within microprocessor 28 or other component of IMD 10, or combination thereof. The successive cardiac episode data includes, for example, electrograms, marker channel diagrams, decision rule outcomes, rate of the cardiac episode, regularity of the cardiac episode, voltage of delivered therapy, number of delivered shocks, or the like. However, successive cardiac episode data can further include morphologies of electrograms, activity level of the patient, lead impedance measurements, pressures measured within the heart, presence of ischemia or edema before, after or during the cardiac episode, absence of ischemia or edema before, after or during the cardiac episode, P-waves and R-waves. Microprocessor 28 assigns the cardiac episode data an initial priority value based on the type of cardiac episode detected. As will be described, microprocessor 28 assigns a ventricular cardiac episode a higher priority value than an atrial cardiac episode due to the fact that ventricular episodes are generally more dangerous to a patient. As another example, microprocessor 28 assigns an atrial electrogram a higher priority value than a ventricular electrogram for an atrial episode.

Microprocessor 28 determines whether memory of IMD 10 The IMD has a memory capacity sufficient to store the received cardiac episode data. When IMD 10 has sufficient memory capacity for storage of the cardiac episode data, microprocessor 28 stores the cardiac episode data in memory, such as RAM 30. Microprocessor 28 further associates an identifier with the stored cardiac episode data, as will be described. When IMD 10 does not have sufficient memory capacity for storage of the cardiac episode data, microprocessor 28 identifies previously stored cardiac episode data with a lowest priority and compares the priority value of the received cardiac episode data to the priority value of previously stored cardiac episode data. If any of the previously stored cardiac episode data has a lower priority than the priority of the new cardiac episode data, microprocessor 28 overwrites the previously stored cardiac episode data with the new cardiac episode data. The new cardiac episode data forms a new base node, or part of an existing branch in the tree for a preexisting episode.

In addition, microprocessor 28 determines whether any priority values associated with previously stored cardiac episode data should be recalculated in light of the received cardiac episode data. Microprocessor 28 recalculates priority values of previously stored cardiac episode data in response to subsequent cardiac events, such as subsequent detection of higher priority cardiac episodes, detection of repeated cardiac episodes, delivery of a therapy to treat the detected cardiac episode, a sudden change in pressure or other hemodynamic parameter, an indication that a patient fell, e.g., from sensors such as accelerometers within IMD10, input received from a patient activator, time frame since the cardiac episode data was detected, length of the episode. Microprocessor 28, for example, receives in put from a patient activator substantially coincident with the particular event indicating that the patient experienced pain and increases the initial priority value of a previously detected cardiac episode.

For instance, if microprocessor 28 detects that a ventricular episode immediately follows an atrial episode, microprocessor 28 increases the priority value of the atrial episode. Further, if IMD 10 delivers a therapy to treat the ventricular episode, microprocessor 24 increases the priority value of the ventricular episode, which also increases the priority of the atrial episode because the two episodes are linked, e.g., the ventricular episode immediately followed the atrial episode. In this manner, the priority values assigned to the cardiac episode data are adaptive, i.e., able to change as more contextual information about an episode becomes available.

Concurrently, microprocessor 28 defines the hierarchical priority relationship, e.g., hierarchical data structure 90, according to the assigned priority values. In other words, as microprocessor 28 receives cardiac data and associates the cardiac data with priority values and data identifiers, microprocessor 28 also develops hierarchical data structure 90. Hierarchical data structure 90 arranges episode and data identifiers, i.e., pointers that point to portions of the stored cardiac episode data, to hierarchically prioritize the cardiac episode data within each of the tree structures as well as among other tree structures. In other words, IMD 10 uses the cardiac episode data received to determine significance of a cardiac episode in relation to other detected cardiac episodes, and within the cardiac episode to determine the relative significance of individual pieces of cardiac episode data.

In response to exceeding a memory capacity threshold, IMD 10 begins to overwrite a portion of the stored cardiac episode data with new cardiac episode data according to the hierarchical priority relationship and, more particularly, according to hierarchical data structure 90. IMD 10 identifies a portion of the stored cardiac episode data with a lowest priority from hierarchical data structure 90, and overwrites the identified portion of the stored cardiac episode data with the new cardiac episode data when the priority value of the new cardiac data exceeds the priority value of the previously stored cardiac data. Upon overwriting previously stored cardiac episode data, microprocessor 28 redefines the hierarchical priority relationships.

As will be described, IMD 10 overwrites portions of the trees, e.g., branches, or entire trees depending on the amount of memory needed and the amount of time between interrogations of IMD 10. For example, IMD 10 can retain cardiac episode data of the initial detection and therapy, eliminate cardiac episode data associated with a middle section of therapies that were applied and failed, and keep cardiac episode data associated with the last therapy and the termination of the episode. IMD 10 and, more particularly, microprocessor 28 applies an algorithm to determine which branches or trees to overwrite, i.e., determine the cardiac episode data with the lowest priority. The algorithm takes into account not only the priority score assigned to the episode node 94, but also the priority value assigned to the associated base node 92. Further, the algorithm takes into account the tiers on which each of the nodes (both episode nodes 94 and base nodes 92) are located. For instance, the algorithm executed by microprocessor 28 counts the priority value of base nodes 92, e.g., nodes on TIER 1 for a larger percentage than the priority value of episode nodes 94, e.g., nodes on TIER 2. In other words, the base nodes 92 are weighted more heavily than episode nodes 94.

Alternatively, or in addition, microprocessor 28 compresses a portion of the stored cardiac episode data in order to store the received cardiac episode data. Microprocessor 28 determines whether the cardiac data with the lowest priority can be compressed to reduce resolution and, in turn, reduce memory space such that the new cardiac episode data can be stored. Microprocessor 28, for example, can compress an electrogram signal and store the reduced resolution electrogram to increase the available memory space for received cardiac episode data. In this manner, the IMD retains as much uncompressed data as possible, but stores the lower priority data with a lower resolution, i.e., greater compression.

Depending on when a physician interrogates IMD 10, the information stored by IMD 10 varies significantly. For example, if the physician interrogates IMD 10 shortly after the last time IMD 10 was interrogated, there is a large amount of detailed information available. In this case IMD 10 can collect extra information including episode data for normal sinus rhythms, all A—A intervals and V—V intervals, or the like. This might be similar to information seen in a Holter recording, except the information is prioritized in accordance with assigned priority scores. However, if the physician does not interrogate IMD 10 for a longer period of time, e.g., a year, much of the detailed information has been overwritten, but there is still overview information available, as well as some detailed information about the most critical events. For example, perhaps many of the cardiac episodes have been completely overwritten, others would contain only the time and final outcome, e.g., diagnostic decision, other cardiac episodes would contain event markers and decision information, and one episode, wherein a shock was given, might contain an electrogram signal, all the markers, and all the decision information. Thus the final result is that IMD 10 optimizes the memory to provide the most relevant information needed for understanding the medical condition of the patient and for improving future treatment.

Further, IMD 10, when interrogated, sends all or a portion of the stored cardiac episode data to the programmer or monitor in accordance with the hierarchical priority relationship. In other words, IMD 10 transmits the stored cardiac episode data with the highest priority to the programmer first followed by the stored cardiac episode data with a lower priority. In this manner, IMD 10 provides the physician or other reviewer with the most relevant cardiac episode data first. IMD 10 can further include a mechanism for tracking which cardiac episode data has been transferred. Upon transmitting the cardiac episode data, IMD 10 reduces the priority values of the cardiac episode data that has been transmitted to the programmer thereby allowing it to be overwritten as new cardiac episode data is received. This way, cardiac episode data with lower initial priority values are stored because the higher priority cardiac episode data has already been transmitted to the programmer.

Figure 4:
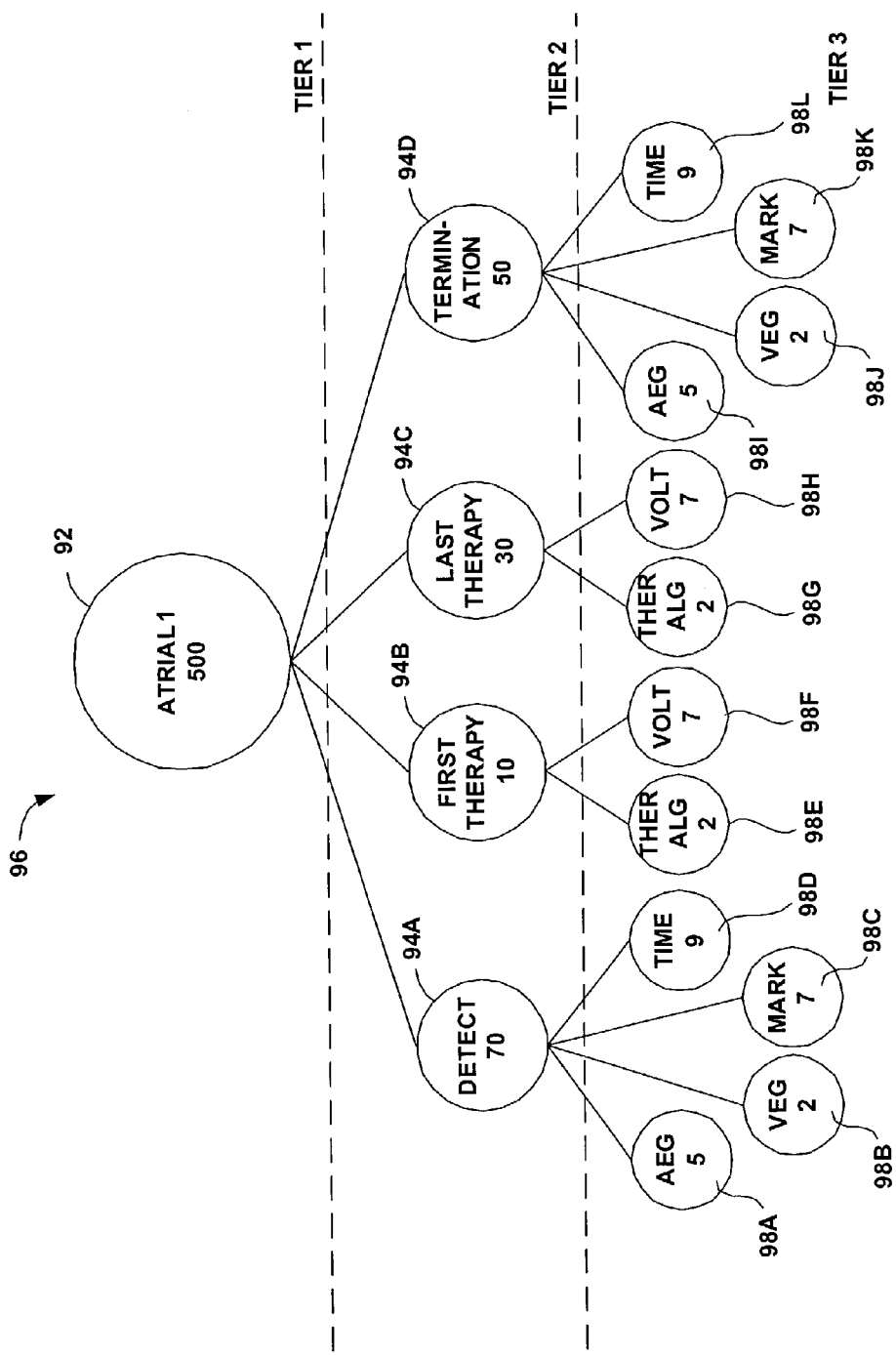
FIG. 4 is a schematic diagram illustrating a portion of the hierarchical data structure of FIG. 3 with three tiers of hierarchical prioritization.

FIG. 4 is a schematic diagram illustrating a portion of hierarchical data structure 90 of FIG. 3 with three tiers of hierarchical prioritization. The portion of hierarchical data structure 90 illustrated in FIG. 4 is a tree structure 96 for an atrial episode, which has a corresponding base node 92A (ATRIAL 1). Tree structure 96 associated with the detected atrial episode includes episode nodes 94A–94D (hereinafter 94) that form "branches" of a root node, i.e., base node 92A. Tree structure 96 of the atrial episode further includes episode sub-nodes 98A–98L (hereinafter 98) that form branches of each of episode nodes 94.

As described above, base node 92A corresponds to a detected cardiac episode and, more particularly, to cardiac episode data associated with the detected cardiac episode. The cardiac episode includes any sort of cardiac episode that originates in the atrium or ventricles of the heart. In the example of FIG. 4, the cardiac episode comprises an atrial episode such as an atrial tachycardia, atrial fibrillation, atrial flutter or the like.

Episode nodes 94 correspond to portions of the cardiac episode data of the particular cardiac episode associated with base node 92 of TIER 1. In the example illustrated in FIG. 4, episode nodes 94 correspond to cardiac episode data at different time intervals during the detected atrial episode. Specifically, episode nodes 94A–94D correspond to cardiac episode data associated with detection of the cardiac episode (DETECT), application of a first therapy (FIRST THERAPY), application of a last therapy (LAST THERAPY) and termination of the detected cardiac episode (TERMINATION), respectively.

Episode sub-nodes 98 correspond to more specific portions of episode data than episode nodes 94. Episode sub-nodes can, for example, correspond to electrograms (atrial, ventricular, or both), marker channel diagrams, decision rule outcomes, rate of the cardiac episode, regularity of the cardiac episode, voltage of delivered therapy, number of delivered shocks, or the like. Further, episode sub-nodes can correspond to morphologies of electrograms, activity level of the patient, lead impedance measurements, pressures measured within the heart, presence of ischemia or edema before, after or during the cardiac episode, absence of ischemia or edema before, after or during the cardiac episode, P-waves and R-waves. In the example illustrated in FIG. 4, episode sub-nodes 98A–98D and 98I–98L associated with episode nodes 94A and 94D, respectively, correspond to atrial electrogram (AEGs), ventricular electrograms (VEGs), marker channel diagrams (MARK), and timestamps (TIME). Episode sub-nodes 98E–98F and 98G–98H correspond to therapy algorithm result (THER ALG) and voltage of the delivered therapy (VOLT).

Base nodes 92, episode nodes 94, and episode sub-nodes 98 include identifiers that associate the nodes with at least a portion of cardiac episode data stored in memory of IMD 10. Base nodes 92 include episode identifiers that correspond to all cardiac episode data of the detected cardiac episode, episode nodes 94 include data identifiers that correspond to a portion of the cardiac episode data of the detected cardiac episode, and episode sub-nodes 98 correspond to a smaller portion of cardiac episode data of the detected cardiac episode. In this manner, each descending tier of the hierarchy corresponds to a more specific portion of cardiac episode data. In the example of FIG. 4, base node 92 corresponds to all of the cardiac episode data of the atrial episode, episode nodes 94 correspond to cardiac episode data at different time intervals of the atrial episode, e.g., detection, and episode sub-nodes 98 correspond to specific cardiac episode data of the corresponding time interval, e.g., electrograms at detection.

Additionally, base nodes 92, episode nodes 94, and episode sub-nodes 98 include associated priority values as well as the identifiers. As described above, the priority values of the nodes are adaptive, i.e., able to change as more contextual information becomes available. The priority values of base nodes 92, episode nodes 94 and episode sub-nodes 98 are initially assigned by microprocessor 28 based on the type of cardiac episode detected. In some embodiments, microprocessor 28 assigns priorities values to the nodes in accordance with information programmed by a physician. For example, the physician may want microprocessor 28 to store particular information necessary for diagnoses of a patient problem. As described above, microprocessor 28 can recalculate initial priority values based on subsequent events. For instance, microprocessor increases an initial priority value assigned to cardiac episode data if a therapy, such as a defibrillation shock, is given before the heart naturally return to normal sinus rhythm. Also, microprocessor increases the initial priority value assigned to cardiac episode data if a subsequent episode quickly follows the first episode.

Microprocessor 28 uses the priority values assigned to cardiac episode data associated with base nodes 92 along with priority values assigned to episode nodes 94, episode sub-nodes 98 and any other lower level nodes to determine priority relationships, which are used when microprocessor 28 overwrites previously stored cardiac episode data due to lack of sufficient memory capacity. More specifically, microprocessor 28 executes an algorithm to determine the cardiac episode data with the lowest priority. As described above, the algorithm can take into account not only the priority score assigned to the node of interest, e.g., episode sub-node 98A, but also the priority value assigned to the associated base node 92 and episode node 94A.

Further, the algorithm takes into account the tiers on which each of the nodes (both episode nodes 94 and base nodes 92) are located. For instance, the algorithm executed by microprocessor 28 weighs the priority value of base nodes 92, e.g., nodes on TIER 1 more than the priority value of episode nodes 94, e.g., nodes on TIER 2 and so on descending down the hierarchy. IMD 10 starts by overwriting the parts of the cardiac episode data associated with a cardiac episode with the lowest priority. As space becomes scarcer, however, IMD 10 overwrites entire cardiac episodes, with episodes of lower priority being overwritten first.

Figure 5:
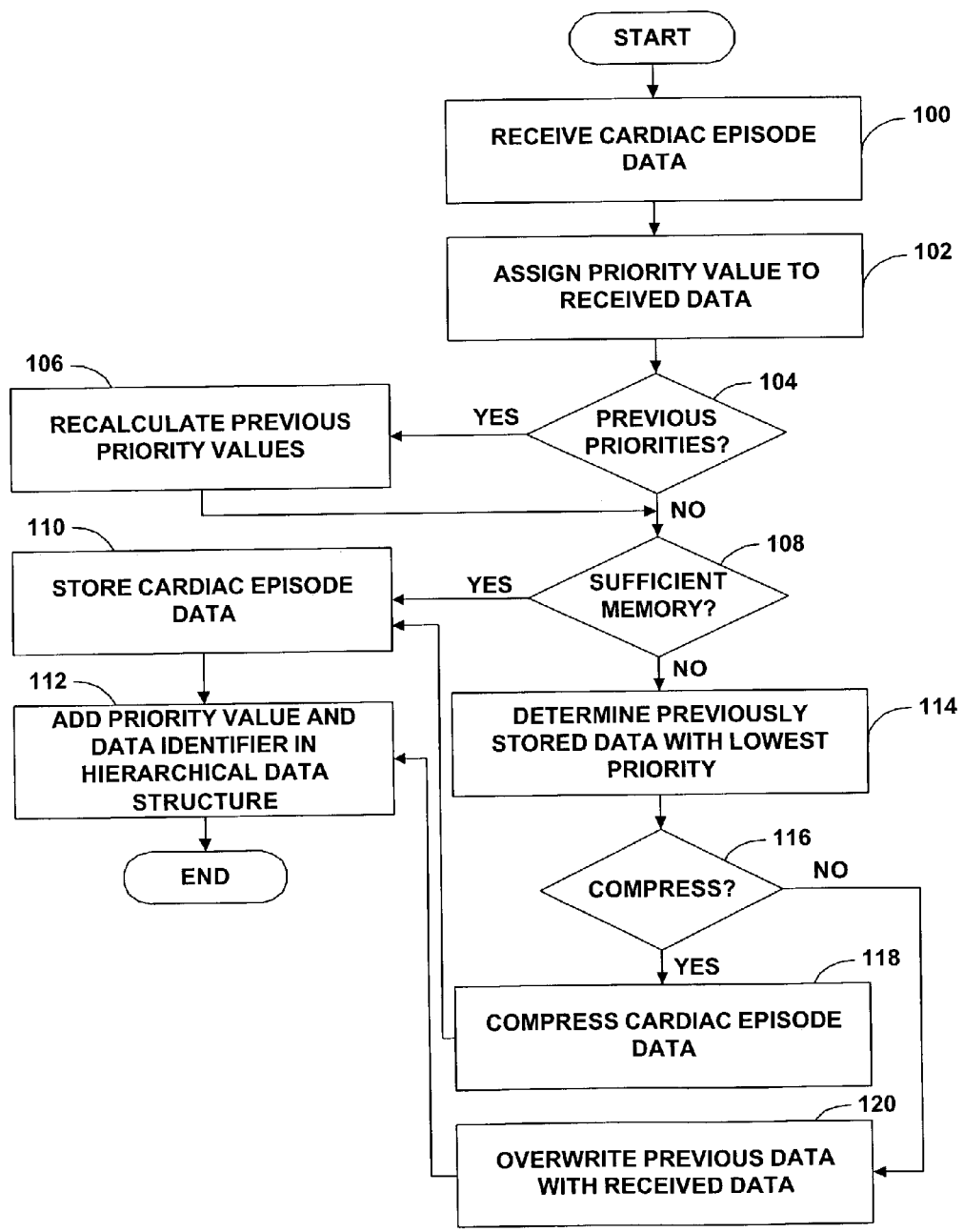
FIG. 5 is a flow diagram illustrating exemplary operation of an IMD selectively storing cardiac episode data in accordance with the invention.

FIG. 5 is a flow diagram illustrating exemplary operation of IMD 10 selectively storing cardiac episode data in accordance with the invention. Initially, microprocessor 28 receives cardiac episode data (100). Microprocessor 28 receives cardiac episode data from sensing electrodes, such as electrodes 34, 36, 42, 44, 50 and 52 (FIG. 2). Microprocessor 28 further receives cardiac episode data from processes executing within microprocessor 28, such as a process that determines detection of a cardiac episode or whether to deliver a therapy to treat the cardiac episode. The cardiac episode data includes, for example, atrial and ventricular electrograms, marker channel diagrams, decision rule outcomes, rate of the cardiac episode, regularity of the cardiac episode, voltage of delivered therapy, number of delivered shocks, morphologies of electrograms, activity level of the patient, lead impedance measurements, pressures measured within the heart, presence of ischemia or edema before, after or during the cardiac episode, absence of ischemia or edema before, after or during the cardiac episode, P-waves and R-waves. Each piece of cardiac episode data is time stamped to aid in prioritization. For example, in some embodiments, IMD 10 assigns newer cardiac episode data a higher priority or reduce the priority of cardiac episode data recorded in the past.

Microprocessor 28 assigns a priority value to the received cardiac episode data (102). Microprocessor 28 assigns the received cardiac episode data an initial priority value based on the type of cardiac episode detected. If the cardiac episode data is a newly detected cardiac episode, e.g., results of a detection algorithm, microprocessor 28 assigns a higher priority value to a ventricular cardiac episode than an atrial cardiac episode. If the cardiac episode data is additional cardiac episode data for a previously detected episode, microprocessor 28 assigns the cardiac episode data different values depending on the importance of the cardiac episode data in relation to the particular detected episode to which the cardiac episode data is associated. For example, if the detected cardiac episode is a ventricular cardiac episode, microprocessor 28 assigns an atrial electrogram a lower priority value than a ventricular electrogram. Microprocessor 28 can further be programmed to assign priority values based on information programmed by a physician. For example, the physician can program IMD 10 and, more particularly, microprocessor 28 to assign higher priority values to particular pieces of cardiac episode data, which are necessary for the physician to diagnose of a problem of the patient.

Microprocessor 28 determines whether the received cardiac episode data affects the priority values assigned to previously stored cardiac episode data (104). As described above, the priority values assigned to previously stored cardiac episode data are adaptive, i.e., can be changed as more contextual information become available. In other words, the priority values assigned to the previously stored cardiac episode data change in response to subsequent events. For example, microprocessor 28 increases the priority value assigned to a cardiac episode when a therapy is delivered to treat the cardiac episode. In another example, microprocessor 28 increases the priority value of an atrial episode when microprocessor 28 detects a subsequent ventricular episode, i.e., an episode of higher priority. Other events that cause microprocessor 28 to recalculate the priority value assigned to the cardiac episode data include detection of repeated cardiac episodes, a sudden change in pressure or other hemodynamic parameter, an indication that a patient fell, e.g., from sensors such as accelerometers within IMD10, input received from a patient activator, time frame since the cardiac episode data was detected, and length of the episode. For example, when microprocessor 28 detects a cardiac episode that is substantially similar to a previously detected cardiac episode, microprocessor 28 assigns the detected cardiac episode a lower priority because similar cardiac episode data is already available. Microprocessor 28, however, would store an annotation to indicate the number of similar episodes that occurred.

When microprocessor 28 determines the received cardiac episode data does affect the priority value assigned to previously stored cardiac episode data, microprocessor 28 recalculates the priority value of the respective previously stored cardiac data (106). As described above, microprocessor 28 increases the priority value assigned to a cardiac episode when a therapy is delivered to treat the cardiac episode.

When microprocessor 28 determines the received cardiac episode data does not affect the priority value assigned to previously stored cardiac episode data or after microprocessor 28 recalculates the priority values of the respective previously stored cardiac data, microprocessor 28 determines whether IMD 10 has sufficient memory capacity to store the received cardiac episode data (108). Microprocessor 28, for example, determines whether the available memory capacity exceeds a memory capacity threshold.

When microprocessor 28 determines there is sufficient memory capacity for storing the received cardiac episode data, microprocessor 28 stores the received cardiac episode data (110). Microprocessor 28 determines, for example, that there is sufficient memory capacity when the memory capacity is below 70% full. Microprocessor 28 further adds the prioritization value assigned to the received cardiac episode data along with a data identifier to hierarchical data structure 90 that defines a hierarchical relationship among the stored cardiac episode data (112).

When microprocessor 28 determines there is not sufficient memory capacity for storing the received cardiac episode data, microprocessor 28 begins to selectively store cardiac episode data. Microprocessor 28, for example, begins to selectively store cardiac episode data when the memory capacity exceeds 70% full. Microprocessor 28 determines previously stored cardiac episode data with the lowest priority (114). As described above, microprocessor 28 applies an algorithm to determine which branches or trees of hierarchical data structure 90 to overwrite. The algorithm takes into account not only the priority score assigned to the cardiac episode data, but also the priority value assigned to cardiac episode data associated with a higher-level tier. Using FIG. 4 as an example, the algorithm takes into account not only the priority score assigned to cardiac data associated with episode sub-node 98A, but also the priority value assigned to cardiac data associated with a respective base node 92 and episode node 94A. Further, the algorithm takes into account the tiers on which each of the nodes (both episode nodes 94 and base nodes 92) are located. For instance, the algorithm executed by microprocessor 28 weights the priority value of base nodes 92, e.g., nodes on TIER 1 more heavily than the priority value of episode nodes 94, e.g., nodes on TIER 2. In some cases, the received cardiac episode data has a lower priority than the cardiac episode data stored in memory.

Microprocessor 28 determines whether the cardiac data with the lowest priority can be compressed, i.e., reduce resolution, in order to free enough memory space such that the new cardiac episode data can be stored (116). Microprocessor can compress previously stored cardiac episode data, received cardiac episode data, or both. When microprocessor 28 determines it can compress cardiac episode data to free enough memory space to store the new cardiac episode data, microprocessor 28 compresses the cardiac episode data with the lowest priority and stores the new cardiac episode data (118, 112). Microprocessor 28, for example, compresses an electrogram signal and stores the reduced resolution electrogram in order to increase the available memory space. In this manner, the IMD retains as much uncompressed data as possible, but stores the lower priority data with a lower resolution, i.e., greater compression. In some embodiments, microprocessor 28 compresses more than one piece of previously stored cardiac episode data.

When microprocessor 28 determines that compression of the cardiac episode data with the lowest priority will not free enough memory space to store the new cardiac episode data, microprocessor 28 overwrites the previously stored cardiac episode data with the lowest priority with the new cardiac episode data (120). Microprocessor 28 further adds the prioritization value assigned to the received cardiac episode data along with a data identifier to hierarchical data structure 90 that defines a hierarchical relationship among the stored cardiac episode data (112).

Various embodiments of the invention have been described. These and other embodiments are within the scope of the following claims.

The invention claimed is:

1. A method comprising:
   assigning cardiac episode data initial priority values;
   storing the cardiac episode data in a memory associated with an implanted medical device;
   recalculating at least one of the initial priority values assigned to the cardiac episode data in response to subsequent cardiac episode data; and
   overwriting a portion of the stored cardiac episode data with new cardiac episode data according to a hierarchical priority relationship and the priority values.

2. The method of claim 1, wherein said overwriting a portion of the stored episode data includes overwriting a portion of the stored episode data according to a hierarchical data structure that represents the hierarchical priority relationship.

3. The method of claim 2, wherein the hierarchical data structure includes a base node for a detected cardiac episode, the base node having an episode identifier and an associated priority value, and one or more episode nodes having data identifiers and associated priority values, wherein the data identifiers correspond to portions of the cardiac episode data of the detected cardiac episode.

4. The method of claim 3, wherein the data identifiers correspond to at least one of cardiac episode detection data, cardiac episode therapy data, and cardiac episode termination data.

5. The method of claim 3, wherein the data identifiers correspond to at least one of an electrogram, a marker channel diagram, a decision rule outcome, a rate of the cardiac episode, regularity of the cardiac episode, a voltage of delivered therapy, number of delivered shocks, morphologies of electrograms, activity level of the patient, lead impedance measurements, pressures measured within the heart, presence of ischemia or edema before, after or during the cardiac episode, absence of ischemia or edema before, after or during the cardiac episode, P-waves and R-waves.

6. The method of claim 3, further comprising one or more episode sub-nodes having data identifiers and associated priority values, wherein the data identifiers of the episode sub-nodes correspond to more specific portions of the cardiac episode data than the data identifiers of the episode node.

7. The method of claim 6, wherein said overwriting a portion of the stored cardiac episode data with new cardiac episode data includes overwriting the portion of the stored cardiac episode data associated with one of the base node, the episode node, and the episode sub-node.

8. The method of claim 2, wherein the hierarchical data structure includes a plurality of base nodes for detected cardiac episodes, each of the base nodes having an episode identifier and an associated priority value, and one or more episode nodes corresponding to each of the base nodes having data identifiers and associated priority values, wherein the data identifiers correspond to portions of the cardiac episode data of the detected cardiac episode.

9. The method of claim 1, wherein said overwriting the data according to the hierarchical relationship comprises:
   identifying at least a portion of the stored cardiac episode data with a lowest priority from the hierarchical priority relationship; and
   overwriting the identified portion of the stored cardiac episode data with the new cardiac episode data when the priority value of the new cardiac episode data exceeds a priority value of the identified portion of the stored cardiac episode data.

10. The method of claim 1, further comprising compressing at least a portion of the new cardiac episode data to reduce necessary memory space.

11. The method of claim 1, further comprising compressing at least a portion of the cardiac episode data stored in the memory to increase available memory space.

12. The method of claim 1, wherein assigning cardiac episode data initial priority values includes assigning cardiac episode data initial priority values based on a type of cardiac episode associated with the cardiac episode data.

13. The method of claim 1, wherein the subsequent cardiac episode data comprises cardiac episode data that indicates successive detection of a higher priority cardiac episode.

14. The method of claim 1, wherein the subsequent cardiac episode data includes cardiac episode data that indicates delivery of a therapy by the implanted medical device to treat the cardiac episode.

15. The method of claim 1, wherein the subsequent cardiac episode data includes cardiac episode data that indicates at least one of detection of repeated cardiac episodes, a sudden change in pressure, an indication that a patient fell, input received from a patient activator, and length of the cardiac episode.

16. The method of claim 1, wherein said overwriting at least a portion of previous cardiac episode data comprises overwriting at least a portion of previous cardiac episode data in response to exceeding a memory capacity threshold.

17. The method of claim 16, wherein exceeding the memory capacity threshold includes reaching a maximum memory capacity.

18. The method of claim 1, further comprising:
   transmitting at least a portion of the stored cardiac episode data to an interrogation device; and
   reducing the priority value of the portion of the cardiac episode data transmitted to the interrogation device.

19. The method of claim 1, further comprising transmitting at least a portion of the stored cardiac episode data to an interrogation device according to the hierarchical priority relationship.

20. A computer-readable medium comprising instructions that cause a processor to:
   assign cardiac episode data initial priority values;
   store the cardiac episode data in a memory associated with an implanted medical device;
   recalculate at least one of the initial priority values assigned to the cardiac episode data in response to subsequent cardiac episode data; and
   overwrite a portion of the stored cardiac episode data with new cardiac episode data according to a hierarchical priority relationship and priority values.

21. The computer-readable medium of claim 20, wherein instructions that cause the processor to overwrite a portion of the stored episode data includes instructions that cause the processor to overwrite a portion of the stored episode data according to a hierarchical data structure that represents the hierarchical priority relationship.

22. The computer-readable medium of claim 21, wherein the hierarchical data structure includes a base node for a detected cardiac episode, the base node having an episode identifier and an associated priority value, and one or more episode nodes having data identifiers and associated priority values, wherein the data identifiers correspond to portions of the cardiac episode data of the detected cardiac episode.

23. The computer-readable medium of claim 20, further comprising instructions that cause the processor to:
   identify at least a portion of the stored cardiac episode data with a lowest priority from the hierarchical priority relationship; and
   overwrite the identified portion of the stored cardiac episode data with the new cardiac episode data when the priority value of the new cardiac episode data exceeds a priority value of the identified portion of the stored cardiac episode data.

24. The computer-readable medium of claim 20, further comprising instructions that cause the processor to compress at least a portion of the new cardiac episode data to reduce necessary memory space.

25. The computer-readable medium of claim 20, further comprising instructions that cause the processor to compress at least a portion of the cardiac episode data stored in the memory to increase available memory space.

26. The computer-readable medium of claim 20, wherein instructions that cause the processor to assign cardiac episode data initial priority values includes instructions that cause the processor to assign cardiac episode data initial priority values based on a type of cardiac episode associated with the cardiac episode data.

27. The computer-readable medium of claim 20, wherein instructions that cause the processor to overwrite at least a portion of previous cardiac episode data comprises instructions that cause the processor to overwrite at least a portion of previous cardiac episode data in response to exceeding a memory capacity threshold.

28. The computer-readable medium of claim 20, further comprising instruction that cause the processor to:
   transmit at least a portion of the stored cardiac episode data to an interrogation device; and reduce the priority value of the cardiac episode data transmitted to the interrogation device.

29. The computer-readable medium of claim 20, further comprising instruction that cause the processor to transmit at least a portion of the stored cardiac episode data to an interrogation device according to the hierarchical priority relationship.

30. An implantable medical device comprising:
a memory to store cardiac episode data; and
a processor to assign cardiac episode data initial priority values, store the cardiac episode data in the memory, recalculate at least one of the initial priority values assigned to the cardiac episode data in response to subsequent cardiac episode data, and overwrite a portion of the stored cardiac episode data with new cardiac episode data according to a hierarchical priority relationship and priority values.

31. The device of claim 30, wherein the processor overwrites a portion of the stored episode data according to a hierarchical data structure that represents the hierarchical priority relationship.

32. The device of claim 31, wherein the hierarchical data structure includes a base node for a detected cardiac episode, the base node having an episode identifier and an associated priority value, and one or more episode nodes having data identifiers and associated priority values, wherein the data identifiers correspond to portions of the cardiac episode data of the detected cardiac episode.

33. The device of claim 32, wherein the data identifiers correspond to at least one of cardiac episode detection data, cardiac episode therapy data, and cardiac episode termination data.

34. The device of claim 32, wherein the data identifiers correspond to at least one of an electrogram, a marker channel diagram, a decision rule outcome, a rate of the cardiac episode, regularity of the cardiac episode, a voltage of delivered therapy, and number of delivered shocks.

35. The device of claim 32, further comprising one or more episode sub-nodes having data identifiers and associated priority values, wherein the data identifiers of the episode sub-nodes correspond to more specific portions of the cardiac episode data than the data identifiers of the episode node.

36. The device of claim 35, wherein the processor overwrites the portion of the stored cardiac episode data associated with at least one of the base node, one of the episode nodes, and one of the episode sub-nodes.

37. The device of claim 30, wherein the hierarchical data structure includes a plurality of base nodes for detected cardiac episodes, each of the base nodes having an episode identifier and an associated priority value, and one or more episode nodes corresponding to each of the base nodes having data identifiers and associated priority values, wherein the data identifiers correspond to portions of the cardiac episode data of the detected cardiac episode.

38. The device of claim 30, wherein the processor identifies at least a portion of the stored cardiac episode data with a lowest priority from the hierarchical priority relationship and overwrites the identified portion of the stored cardiac episode data with the new cardiac episode data when the priority value of the new cardiac episode data exceeds a priority value of the identified portion of the stored cardiac episode data.

39. The device of claim 30, wherein the processor compresses at least a portion of the new cardiac episode data to reduce necessary memory space.

40. The device of claim 30, wherein the processor compresses at least a portion of the cardiac episode data stored in the memory to increase available memory space.

41. The device of claim 30, wherein the processor assigns cardiac episode data initial priority values based on a type of cardiac episode associated with the cardiac episode data.

42. The device of claim 30, wherein the subsequent cardiac episode data comprises cardiac episode data that indicates detection of a subsequent cardiac episode.

43. The device of claim 30, wherein the subsequent cardiac episode data includes cardiac episode data that indicates delivery of a therapy by the implanted medical device to treat the cardiac episode.

44. The device of claim 30, wherein the subsequent cardiac episode data includes cardiac episode data that indicates at least one of detection of repeated cardiac episodes, a sudden change in pressure, an indication that a patient fell, input received from a patient activator, and length of the cardiac episode.

45. The device of claim 30, wherein the processor overwrites at least a portion of previous cardiac episode data in response to exceeding a programmed memory capacity threshold.

46. The device of claim 30, wherein the memory has a maximum memory capacity and the processor overwrites at least a portion of previous cardiac episode data in response to reaching the maximum memory capacity.

47. The device of claim 30, wherein the processor executes at least one algorithm to obtain cardiac episode data.

48. The device of claim 30, wherein the algorithm includes one of a detection algorithm and a therapy decision algorithm.

49. The device of claim 30, further comprising at least one sensing electrode to receive cardiac episode data from a patient.

* * * * *

UNITED STATES PATENT AND TRADEMARK OFFICE
CERTIFICATE OF CORRECTION

PATENT NO. : 7,130,678 B2 Page 1 of 1
APPLICATION NO. : 10/423601
DATED : October 31, 2006
INVENTOR(S) : Ritscher et al.

It is certified that error appears in the above-identified patent and that said Letters Patent is hereby corrected as shown below:

Column 20, line 45 please change "claim 30" to --claim 47--.

Signed and Sealed this

Second Day of October, 2007

JON W. DUDAS
*Director of the United States Patent and Trademark Office*